(12) United States Patent
Iding et al.

(10) Patent No.: US 6,420,166 B2
(45) Date of Patent: Jul. 16, 2002

(54) PROCESS FOR THE PREPARATION OF D-ASPARAGINE DERIVATIVES

(75) Inventors: Hans Iding, Rheinfelden (DE); Mark Rogers-Evans, Binningen; Beat Wirz, Reinach, both of (CH)

(73) Assignee: Basolea Pharmaceutica AG, Binningen (CH)

( * ) Notice: Subject to any disclaimer, the term of this patent is extended or adjusted under 35 U.S.C. 154(b) by 0 days.

(21) Appl. No.: 09/834,129

(22) Filed: Apr. 12, 2001

(30) Foreign Application Priority Data

Apr. 19, 2000 (EP) .............................. 00108542

(51) Int. Cl.$^7$ ................................. C12P 13/20
(52) U.S. Cl. ..................................... 435/280; 435/109
(58) Field of Search .................................. 435/109, 280

(56) References Cited

U.S. PATENT DOCUMENTS

| 2,511,867 A | 6/1950 | Neuberg et al. |
| 4,211,840 A | 7/1980 | Nakamori et al. |

FOREIGN PATENT DOCUMENTS

| EP | 814 296 | 7/1951 |
| EP | 0 182 517 | 5/1986 |
| EP | 0 358 428 | 3/1990 |
| EP | 0 620 225 | 10/1994 |
| EP | 0 849 269 | 6/1998 |
| EP | 0 896 057 | 2/1999 |
| EP | 0 928 787 | 7/1999 |
| EP | 0 950 706 | 10/1999 |
| WO | WO 99/65920 | 12/1999 |

OTHER PUBLICATIONS

Chen et al "Chirally Selective Hydrolysis of D, L–Amino Acid Esters by Alkaline Protease" J.Chem Soc Chem Comm 1986 vol. 20, 1514–1516.*
J. Liq. Chrom. (1994), vol. 17 (13) pp. 2759–2775.
Tetrahedron (1997), 53(6), pp. 2075–2086.
Tetrahedron Asymmetry (1992), vol. 3(10) pp. 1239–1242.
J. Chem. Soc. Perkin Trans. 1(1983), pp. 2287–2291.
Agric. Biol. Chem. (1987), 51(3), pp. 721–728.
Green, T., Protective Groups in Organic Synthesis, John Wiley & Sons, Inc. (1981), pp. 218–287.
Zhang, et al. (1997), J. Org. Chem. vol. 62, pp. 2466–2470.

* cited by examiner

Primary Examiner—Herbert J. Lilling
(74) Attorney, Agent, or Firm—George W. Johnston; Patricia S. Rocha-Tramaloni; Eileen M. Ebel

(57) ABSTRACT

The present invention provides a process for the preparation of D-asparagine derivatives of formula I

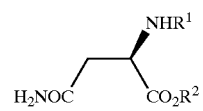

wherein $R^1$ is an amino protecting group and $R^2$ is an alkyl, a substituted alkyl or a group of formula A

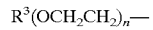

wherein $R^3$ is hydrogen or an lower alkyl group and n is 1, 2 or 3, which process comprises reacting a compound of formula II

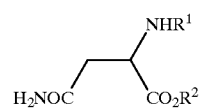

wherein $R^1$ and $R^2$ are as defined above, with a protease in an aqueous solution at a pH of 6.0–7.5 and an organic solvent, and subsequently extracting the enantiomeric pure product of formula I. Compounds of formula I can be used as intermediates in the production of antibacterial substances.

8 Claims, No Drawings

PROCESS FOR THE PREPARATION OF D-ASPARAGINE DERIVATIVES

BACKGROUND OF THE INVENTION

The present invention relates to a new process for the preparation of D-asparagine derivatives of formula I

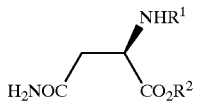

wherein $R^1$ is an amino protecting group and $R^2$ is an alkyl, a substituted alkyl or a group of formula A

wherein $R^3$ is hydrogen or a lower alkyl group and n is 1, 2 or 3.

Compounds of formula I are known. The compound N-benzyloxycarbonyl-D-asparaginemethylester is described in J. Liq. Chrom. (1994), 17 (13), 2759. A chemical synthesis of this compound is described in Tetrahedron (1997), 53 (6), 2075, where it is accomplished by a two-step reaction starting with already chiral (S)-asparagine. In a similar way, as described in Tetrahedron Asymmetry (1992), 3 (10), 1239, N-protected (S)-asparagine methyl ester is prepared in a two-step reaction, starting with already chiral N-protected (S)-asparagine. In J. Chem. Soc. Perkin Trans 1 (1983), 2287 the synthesis of the above-mentioned compound is described, starting also with a chiral reactant.

In EP 0 950 706 and in EP 0 896 057 the production and purification of novel D-aminoacylases from a microorganism belonging to the genus Sebekia or Amycolatopsis, respectively, is described. The enzymes are useful for the industrial production of chiral D-amino acids starting with racemic N-acetyl-D,L-amino acids. The D-aminoacylase (genus Sebekia) has an activity towards N-acetyl-D-asparagine of 1.4% as compared to N-acetyl-D-methionine (100%). The D-aminoacylase (genus Amycolatopsis) has a specific activity towards N-acetyl-D-asparagine of 19% as compared to N-acetyl-D-methionine (100%).

In Agric. Biol. Chem. (1987), 51 (3), 721 and in DE 2825245 the enzymatic preparation of D-amino acids, starting with D,L-5-substituted hydantoin, is described. The synthesis of D-asparagine is accomplished in a two-step reaction ( first: ring opening of D,L-5-substituted hydantoins to D-N-carbamyl amino acids by D-hydantoin hydrolase, followed second by the cleavage of N-carbamyl-D-amino acids to D-amino acids by N-carbamyl-D-amino acid hydrolase using Genus Pseudomonas AJ-1122) or in a one-step reaction using Genus Pseudomonas, Achromobacter, Alcaligenes, Maraxella, Paracoccus or Arthrobacter.

No technical enzymatic reaction for the preparation of asparagine ester derivatives has been described in the literature. This might be due to the ease of racemization and degradation of asparagine derivatives at the conventional pH-values (7–8.5) used for hydrolase reactions. A rapid inactivation of the enzymes was observed when higher, technical, more relevant substrate concentrations were used.

SUMMARY OF THE INVENTION

The present invention provides a process for the preparation of D-asparagine derivatives of formula I

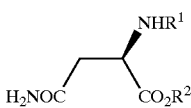

wherein $R^1$ is an amino protecting group and $R^2$ is an alkyl, a substituted alkyl or a group of formula A

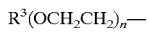

wherein $R^3$ is hydrogen or a lower alkyl group and n is 1, 2 or 3, comprising:

a) reacting a compound of formula II

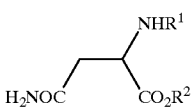

wherein $R^1$ and $R^2$ are as defined above, with a protease in an aqueous solution at a pH of 6.0–7.5 and an organic solvent, and b) extracting the D-asparagine derivative of formula I.

The present invention also provides a process for the preparation of N-protected L-asparagine of formula III

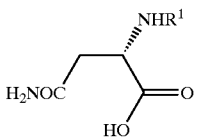

wherein $R^1$ is an amino protecting group and $R^2$ is an alkyl, a substituted alkyl or a group of formula A

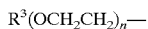

wherein $R^3$ is hydrogen or a lower alkyl group and n is 1, 2 or 3, comprising:

a) reacting a compound of formula II

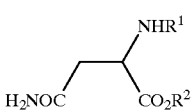

wherein $R^1$ and $R^2$ are as defined above, with a protease in an aqueous solution at a pH of from 6.0–7.5 and an organic solvent, b) extracting a D-asparagine derivative of formula I; and c) treating the aqueous layer from the extraction of step b) to obtain the N-protected L-asparagine of formula III.

DETAILED DESCRIPTION OF THE INVENTION

Surprisingly, it has now been found, that enzyme inactivation during the preparation of asparagine ester derivatives could be overcome by employing an organic solvent. (The effect of the solvent is not that of a "substrate solubilizer" since if it is added after the reaction has come to a stop, the reaction does not resume.) The compounds of formula I can be prepared in an improved way by the process of the present invention. The process of the invention provides for the preparation of D-asparagine derivatives of formula I

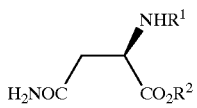

wherein $R^1$ is an amino protecting group and $R^2$ is an alkyl, a substituted alkyl or a group of formula A

wherein $R^3$ is hydrogen or a lower alkyl group and n is 1, 2 or 3, which process comprises reacting a compound of formula II

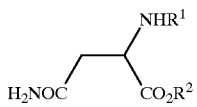

wherein $R^1$ and $R^2$ are as defined above, with a protease in an aqueous system, i.e., an aqueous solution, at a pH of 6.0–7.5 and an organic solvent, and subsequent extraction of the enantiomeric pure product of formula I.

In the structural formulae presented herein a wedged bond (——) denotes that the substituent is above the plane of the paper.

In the structural formulae presented herein a dotted bond (·····) denotes that the substituent is below the plane of the paper.

The term "amino protecting group" as used herein refers to groups such as those employed in peptide chemistry as described in Green, T., Protective Groups in Organic Synthesis, Chapter 5, John Wiley and Sons, Inc. (1981), pp. 218–287, such as an allyloxy-carbonyl group (ALLOC), a lower alkoxycarbonyl group (e.g. tert.-butoxycarbonyl (t-BOC)), a substituted lower alkoxycarbonyl group (e.g. trichloroethoxycarbonyl), an optionally substituted aryloxycarbonyl group (e.g. p-nitrobenzyloxycarbonyl, benzyloxycarbonyl (Z) or phenyloxycarbonyl), an arylalkyl group (e.g. triphenylmethyl (trityl), benzhydryl or benzyl), an alkanoyl group (e.g. formyl, acetyl), an aroyl group (e.g. benzoyl), a halogen-alkanoyl group (e.g. trifluoroacetyl) or a silyl protective group (e.g. tert.-butyldimethylsilyl).

Preferred amino protecting groups are benzyloxycarbonyl, tert.-butoxycarbonyl, allyloxycarbonyl or benzoyl, especially preferred amino protecting group are benzyloxycarbonyl or benzoyl.

The term "alkyl" as used herein denotes straight or branched chain hydrocarbon residues containing 1 to 8 carbon atoms, such as methyl, ethyl, n-propyl, isopropyl, n-butyl, 1-sec-butyl, isobutyl, tert.-butyl, pentyl, hexyl, heptyl, octyl, including their different isomers. Preferably, the term "alkyl" denotes an optionally substituted straight or branched chain hydrocarbon residue containing 1 to 5 carbon atoms.

Alkyl in $R^2$ is preferably methyl, ethyl, n-propyl, isopropyl, n-butyl, 1-sec-butyl, isobutyl or pentyl and more preferred methyl or ethyl.

The term "lower alkyl" as used herein denotes straight or branched chain hydrocarbon residues containing 1 to 4 carbon atoms, such as methyl, ethyl, n-propyl, isopropyl, n-butyl, 1-sec-butyl, isobutyl or tert.-butyl.

The term "substituted alkyl" as used herein denotes a straight or branched chain hydrocarbon residues containing 1 to 8 carbon atoms in which one or more hydrogen atoms are substituted by one or more hydroxy groups, lower alkoxy groups, cycloalkyl groups, aryl groups or by one or more halogen atoms. Examples are 3-hydroxybutyl, 4-methoxybutyl, 3-ethoxypropyl, 3-cyclohexylpropyl, benzyl, 2-phenylethyl, 1-fluoromethyl, 2-chloroethyl, 2,2-dichloroethyl, 3-bromopropyl or 2,2,2-trifluoroethyl and the like.

Substituted alkyl in $R^2$ is preferably benzyl.

The term "cycloalkyl" as used herein denotes a 3–6 membered saturated carbocyclic moiety, e.g. cyclopropyl, cyclobutyl, cyclopentyl or cyclohexyl, preferably cyclohexyl.

The term "lower alkoxy" as used herein denotes a straight or branched chain lower alkyl-oxy group wherein the "lower alkyl" portion is as defined above. Examples are methoxy, ethoxy, n-propyloxy, iso-propyloxy, n-butyloxy, iso-butyloxy or tert.-butyloxy. More preferred lower alkoxy groups within the invention are methoxy or ethoxy.

The term "aryl" as used herein denotes an optionally substituted phenyl group in which one or more aryl hydrogen atoms may be substituted by one or more phenyl groups, alkyl groups, lower alkoxy groups or halogenated alkyl groups. Examples for substituted phenyl groups are biphenyl, o-methylphenyl, m-methylphenyl, p-methylphenyl, o-methoxyphenyl, m-methoxyphenyl, p-methoxyphenyl, o-fluoromethylphenyl, m-fluoromethylphenyl, p-fluoro-methylphenyl, o-chloromethylphenyl, m-chloromethylphenyl, p-chloromethylphenyl, o-bromomethylphenyl, m-bromomethylphenyl or p-bromomethylphenyl.

The term "aryloxy" signifies an aryl group as defined above which is bonded via an oxygen atom. Examples are phenyloxy, benzyloxy and the like.

The term "lower alkoxycarbonyl" denotes lower alkoxy residues attached to a carbonyl group (>C=O). Examples are methoxycarbonyl, ethoxycarbonyl, propoxycarbonyl, tert.-butoxycarbonyl and the like. Preferred lower alkoxycarbonyl is tert.-butoxycarbonyl.

The term "aryloxycarbonyl" denotes aryloxy residues attached to carbonyl group (>C=O). Examples are nitrobenzyloxycarbonyl, benzyloxycarbonyl (Z) or phenyloxycarbonyl.

Aryloxycarbonyl in $R^1$ is nitrobenzyloxycarbonyl, benzyloxycarbonyl (Z) or phenyloxycarbonyl, more preferred benzyloxycarbonyl (Z).

By the term "arylalkyl" as used herein denotes a hydrocarbon group in which one or more alkyl hydrogen atoms are substituted by an aryl group such as trityl, benzhydryl or benzyl.

The term halogen stands for fluorine, chlorine or bromine.

The compounds of formula II may be prepared according to known methods from textbooks on organic chemistry e.g. from J. March (1992), "Advanced Organic Chemistry: Reactions, Mechanisms and Structure"; $4^{th}$ ed. John Wiley and Sons. For example, a N-protected D,L-asparagine derivative is esterified with the corresponding alcohol (e.g. methanol) in the presence of thionylchloride.

According to the invention compounds of formula I are prepared by the reaction of a compound of formula II, wherein $R^1$ and $R^2$ are as defined above, preferably, wherein $R^1$ is benzyloxycarbonyl, tert.-butoxycarbonyl, allyloxycarbonyl or benzoyl and R² is methyl, ethyl, n-propyl, isopropyl, n-butyl, 1-sec-butyl, isobutyl, tert.-butyl, pentyl or benzyl, with a protease in a solution at a pH of 6.0–7.5 in combination with an organic solvent. After the enzymatic hydrolysis of the L-asparagine derivative, the enantiomerically pure D-asparagine derivative of formula I is separated by extraction.

Suitable enzymes as catalysts for the reactions are proteases, preferably inexpensive bulk proteases of microbial origin. More preferred are Bacillus proteases (like Savinase from Novo Nordisk) or subtilisins e.g. subtilisin Carlsberg from Novo Nordisk (Alkalase) or from Solvay (Protease-L).

As an alternative the enzymes may be used in immobilized form.

According to the invention, the reaction is carried out in an aqueous-organic system having an aqueous solution at a pH of 6.0–7.5 and at least one organic solvent. The organic solvent(s) may be water-miscible organic solvent(s) (in a final concentration of up to 25%, preferably 10–25% (v/v)) and/or water-immiscible organic solvent(s) (in any ratio).

As to the aqueous phase, the aqueous solution can be a buffer solution known to be used for biochemical conversions, e.g., a common buffer solution such as sodium or potassium phosphate, used in a concentration of up to 1M, preferably between about 5 mM and about 50 mM. Such a buffer solution may additionally contain one of the usual salts, e.g., sodium or potassium chloride, LiSCN, $Na_2SO_4$ or a polyhydric alcohol, e.g. a sugar, in a concentration up to 1M, preferably 0.1 M. The solution has a pH from 6.0 to 7.5, preferably from 6.0 to 7.0, and especially preferred from 6.4 to 6.6.

The reaction pH ranges from 6.0 to 7.5, preferably the reaction pH ranges from 6.0 to 7.0. An especially preferred reaction pH ranges from 6.4 to 6.6.

Suitable organic solvents are technically common solvents. Examples are ethers (e.g. tetrahydrofuran (THF), dioxan or tert.-butyl methyl ether (TBME)), lower alcohols, esters (e.g. ethyl acetate), polar aprotic solvents (e.g. dimethylsulfoxide (DMSO), dimethyl-acetamide, N,N-dimethylformamide (DMF) or acetone). Preferred are water-miscible organic solvents (e.g. tetrahydrofuran (THF), dioxan, tert.-butyl methyl ether (TBME), lower alcohols, ethyl acetate or acetone).

The term "lower alcohol" as used herein denotes straight or branched chain alkyl residues containing 1 to 8 carbon atoms with one hydroxy group, such as methanol, ethanol, propanol, isopropanol, butanol, isobutanol, tert.-butanol, pentanol, hexanol, heptanol or octanol, preferably methanol, ethanol, propanol, isopropanol, butanol, isobutanol, tert.-butanol and more preferred alcohol's are methanol or ethanol. Most preferred alcohol is ethanol.

The substrate is suitably applied as a suspension in a 5–15% overall concentration (w/w). A more preferred overall concentration is 8–12%.

After addition of the enzyme, the pH of the reaction mixture is maintained under vigorous stirring at the selected pH-value by the controlled addition of a base. Preferred bases are aqueous NaOH or KOH solutions.

After termination of the reaction, the enantiomerically pure product of formula I is worked up conventionally by extraction of the reaction mixture with a suitable organic solvent. A preferred organic solvent is dichloromethane.

Optionally, the remaining aqueous layer could be treated to give the corresponding N-protected L-asparagine. This is achieved conventionally by acidification of the retained aqueous phase and filtering off the formed precipitate or its extraction with a suitable organic solvent.

Therefore, also part of the present invention is a process for the preparation of N-protected L-asparagine of formula III

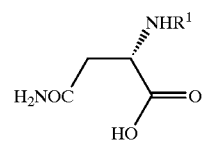

wherein $R^1$ is as defined above, preferably wherein $R^1$ is benzyloxycarbonyl, tert.-butoxycarbonyl, allyloxycarbonyl or benzoyl which process comprises a) reacting a compound of formula II

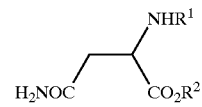

wherein $R^1$ and $R^2$ are as defined above, preferably wherein $R^1$ is benzyloxycarbonyl, tert.-butoxycarbonyl, allyloxycarbonyl or benzoyl and $R^2$ is methyl, ethyl, n-propyl, isopropyl, n-butyl, 1-sec-butyl, isobutyl, pentyl or benzyl with a protease, preferably with a microbial protease, more preferred with a subtilisin or with a Bacillus protease in an aqueous solution at a pH of 6.0–7.5, preferably at a pH of 6.0–7.0 and most preferred at a pH of 6.4–6.6, and an organic solvent. The more preferred organic solvent is tetrahydrofuran, dioxan, tert.-butyl methyl ether, a lower alcohol, ethyl acetate, dimethylsulfoxide, dimethylacetamide, N,N-dimethylformamide or acetone, and most preferred is tetrahydrofuran (THF), dioxan, tert.-butyl methyl ether (TBME), lower alcohols, ethyl acetate or acetone. The mixture is subsequently extracted to obtain the enantiomeric pure product of formula I and the aqueous layer from the extraction is retained; and b) treating the retained aqueous layer to give the corresponding N-protected L-asparagine of formula III.

Optionally, in order to obtain a high chemical purity for the product of formula I or III, it can be triturated in the presence of a suitable organic solvent in which the product of formula I or III is, for reasons of stability, virtually insoluble.

The process is preferably carried out for the preparation of N-benzyloxycarbonyl-D-asparagine methyl ester and triturated in the presence of TBME.

The compounds of formula I, prepared according to the inventive process can be used for the preparation of optically active 3-aminopyrrolidine derivatives of formula IV

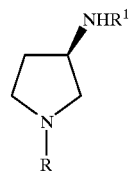

wherein $R^1$ is an amino protecting group and R is hydrogen, $C_{1-12}$-alkyl, $C_{3-8}$-cycloalkyl, $C_{3-12}$-alkenyl, phenyl, tolyl, naphthyl, pyridine, pyrimidine, pyridazine, benzyl, preferably wherein $R^1$ is benzyloxycarbonyl, tert.-butoxycarbonyl, allyloxycarbonyl or benzoyl and R is hydrogen, $C_{1-8}$-alkyl, $C_{3-8}$-cycloalkyl, $C_{3-8}$-alkenyl, phenyl, tolyl, naphthyl, pyridine, pyrimidine, pyridazine, benzyl, and most preferred wherein $R^1$ is benzyloxycarbonyl, tert.-butoxycarbonyl, allyloxycarbonyl or benzoyl and R is benzyl.

The reaction for the preparation of the optically active 3-aminopyrrolidine derivatives of formula IV may be carried out as described in U.S. Pat. No. 5,977,381, which is incorporated herein by reference.

The optically active 3-aminopyrrolidine derivatives of formula IV are important building blocks for the production of useful products in the chemical, agricultural and in the pharmaceutical industry. In particular they are useful for the production of antibacterial substances as for example vinylpyrrolidinone-cephalosporin derivatives as described in WO 99/65920, EP-A 0 620 225 or in EP-A 0 849 269.

In the following examples the abbreviations used have the following significations.

| | |
|---|---|
| ISP-MS | ion spray positive mass spectroscopy |
| ISN-MS | ion spray negative mass spectroscopy |
| EI-MS | electron impact mass spectroscopy |
| SFC | super critical fluid chromatography |
| NMR | nuclear magnetic resonance spectroscopy |
| IR | infra red spectroscopy |
| HV | high vacuum |
| min | minute(s) |

EXAMPLE 1

Preparation of the Reactant

N-Benzyloxycarbonyl-(D,L)-asparagine Methyl Ester 18.85 g (70.8 mmol) of N-benzyloxycarbonyl-(D,L)-asparagine [Bachem] was dissolved/suspended in 230 ml methanol and the solution/suspension was then cooled to 0° C. 16.0 ml of thionylchloride was added dropwise, so that the temperature remained below 10° C. At the end a clear solution was formed which was stirred for 15 min. The reaction mixture was evaporated together with 550 ml toluene (after ca. 150 ml of volume was reached, 100 ml methanol was added and evaporation continued; 40° C. bath temperature). The resulting white, crystalline residue was triturated/digested overnight in 200 ml tert.-butyl methyl ether. The residue was filtered off and dried at HV to give 18.7 g of N-benzyloxycarbonyl-(D,L)-asparagine methyl ester as a white crystalline powder (yield: 92%). ISP-MS: 303.2 (M+Na$^+$), 281.2 (M+H$^+$), 237.2 (M-CO$_2$). SFC: 97.7% area.

EXAMPLE 2

Large Scale Preparation of a Product

N-Benzyloxycarbonyl-D-asparagine Methyl Ester 18.5 g (65.7mmol) of N-benzyloxycarbonyl-(D,L)-asparagine methyl ester (99.5%) was suspended in 190 ml 0.1M sodium chloride solution, 40 ml 0.1M sodium phosphate buffer pH 6.5 and 25 ml THF under vigorous stirring. 1.0 ml Alkalase 2.4 L [a subtilisin Carlsberg from Novo Nordisk] was added and the pH was maintained at 6.5 under vigorous stirring by the controlled addition (pH-static) of 1.0 N sodium hydroxide solution. After a consumption of 32.0 ml of 1.0 N sodium hydroxide solution (16.3 h; 49% conversion after 8 h) the reaction mixture was extracted with 3×350 ml dichloromethane. The combined organic phases were washed briefly with 500 ml 20 mM sodium phosphate buffer pH 7.0, dried on anhydrous sodium sulfate and evaporated (at 25° C. bath temperature). The residue was triturated overnight in 200 ml tert.-butyl methyl ether. The suspension was filtered and the filter cake dried at HV to give 8.2 g N-benzyloxycarbonyl-D-asparagine methyl ester as a white crystalline powder (yield: 46%). Enantiomeric excess: >99.5% (Chiracel ODH, 15 cm×300 μm, 85% n-hexane+15% isopropanol, 6 μl/min, 0.5 MPa, 30° C., 210 nm). EI-MS: 280.2 (M), 221.1 (M-CO$_2$Me). SFC: 98.8% area. IR (Nujol): 3349, 1741, 1665, 1550, 733, 698 cm$^{-1}$. $^1$H-NMR (CDCl3): 2.76 (dd, J$_1$=4 Hz, J$_2$=16 Hz, 1H, —CHCH—), 2.98 (dd, J$_1$=4 Hz, J$_2$=16 Hz, 1H, —CHCH—), 3.76 (s, 3H, OCH$_3$),4.60 (m, 1H, —CHCOO—), 5.13 (s, 2H, —CH$_2$O), 5.42 and 5.53 (2×bs, 2H, CONH$_2$),6.00 (bd, <1H, OCONH), 7.29–7.37 (stack, 5H, Ph).

EXAMPLE 3

Small Scale Preparation of a Product with Different Proteases

N-Benzyloxycarbonyl-D-asparagine Ethyl Ester 0.5 g (1.7 mmol) of N-benzyloxycarbonyl-(D,L)-asparagine ethyl ester (prepared in analogy to example 1) was suspended under vigorous stirring in 23 ml 0.1M sodium chloride solution and 2 ml 0.1M sodium phosphate buffer pH 7.0 in the presence or absence of 4 ml tetrahydrofuran (THF). The pH was adjusted to 6.5 with 1.0N hydrochloric acid and the reaction started by addition of the protease (name, origin and amount see below table). The pH was maintained at 6.5 under vigorous stirring by the controlled addition (pH-static) of 1.0 N sodium hydroxide solution. The experiments without THF showing incomplete conversion (see below table) were not worked up, the experiments with THF were treated as follows: After approximately 50% conversion (corresponds to a consumption of 0.85 ml of 1.0N sodium hydroxide solution) the reaction mixture was extracted with 2×25 ml dichloromethane. The combined organic phases were dried on anhydrous sodium sulfate and evaporated (at 35° C. bath temperature). The residue containing the retained ester was subjected to ee-determination (Chiracel ODH, 15 cm×2.1 mm, 87% n-heptane+13% isopropanol+0.1% TFA, 0.1 ml/min, r.t., 220 nm).

| enzyme | | THF | conversion | time (h) | e.e. of ester |
|---|---|---|---|---|---|
| Savinase 16 L from *Bacillus sp.* | 50 μl | — | 19% | reaction stops, no workup | |
| (Novo) | 50 μl | 4 ml | 53% | 2.8 | 98.5% |
| Protease K from *Tritirachium album* | 4.0 mg | — | 7% | reaction stops, no workup | |
| (Fluka 82495) | 4.2 mg | 4 ml | 48% | 3.2 | 96.7% |
| Protease from *Streptomyces griseus* | 4.0 mg | — | 5% | reaction stops, no workup | |
| (Sigma P-5147) | 4.0 mg | 4 ml | 48% | 12 | 92.1% |

EXAMPLE 4

Large Scale Preparation of a Product Including Subsequent Work-up to Yield also to N-benzyloxycarbonyl-L-asparagine N-Benzyloxycarbonyl-D-asparagine Ethyl Ester 10.0 g (34.0 mmol) of N-benzyloxycarbonyl-(D,L)-asparagine ethyl ester (prepared in analogy to example 1)

was suspended under vigorous stirring in 460 ml 0.1M sodium chloride solution and 40 ml 0.1M sodium phosphate buffer pH 7.0 in the presence of 80 ml tetrahydrofuran. The pH was adjusted to 6.5 with 1.0N hydrochloric acid and the reaction started by addition of 1.0 ml Savinase 16 L [a Bacillus protease from Novo Nordisk]. The pH was maintained at 6.5 under vigorous stirring by the controlled addition (pH-static) of 1.0N sodium hydroxide solution. After a consumption of 16.45 ml 1.0N sodium hydroxide solution (48.2% conversion; after 17 h) the reaction mixture was extracted with 2×500 ml dichloromethane. The combined organic phases were dried on anhydrous sodium sulfate, evaporated (at 35° C. bath temperature) and the residue dried on HV to give 5.02 g of N-benzyloxycarbonyl-D-asparagine ethyl ester as white crystals (yield: 50%). Enantiomeric excess: 98.9% (Chiracel ODH, 15 cm×2.1 mm, 87% n-heptane+13% isopropanol+0.1% TFA, 100 µl/min, r.t., 220 nm). $[\alpha]_D$=+12.2°(c=1.0; EtOH). ISP-MS: 317.2 (M+Na$^+$), 295.3 (M+H$^+$). HPLC: >99% area. $^1$H-NMR (DMSO): 1.16 (t, 3H, CH$_3$),2.42–2.58 (stack, ~2H, —CH$_2$—),4.07 (m, 2H, —CH$_2$O—),4.39 (m, 1H, —CH—), 5.03 (m, 2H, —CH$_2$O—),6.93 (bs, 1H, CONH$_2$), 7.31–7.37 (stack, 6H, Ph and CONH$_2$),7.60 (d, 1H, —CONH—).

N-benzyloxycarbonyl-L-asparagine

The aqueous phase was acidified to pH 2 with 25% hydrochloric acid and extracted with 2×500 ml dichloromethane. The combined organic phases were dried on anhydrous sodium sulfate, evaporated and the residue dried on HV to give 3.13 g of N-benzyloxy-carbonyl-L-asparagine as white crystals (yield: 34%). Enantiomeric excess: >99% (Chiracel ODH, 15 cm×2.1 mm, 87% n-heptane+13% isopropanol+0.1% TFA, 100 µl/min, r.t., 220 nm). $[\alpha]_D$=−6.7°(c=1.1; DMSO). ISP-MS: 289.2 (M+Na$^+$), 267.0 (M+H$^+$). HPLC: >99% area. $^1$H-NMR (DMSO): 2.41–2.58 (stack, 2H, —CH$_2$—),4.34 (m, 1H, —CH—), 5.03 (s, 2H, —OCH$_2$—),6.92 (bs, 1H, CONH$_2$), 7.35 (bs, 6H, Ph and CONH$_2$), 7.45 (d, 1H, —CONH—), 12.6 (s, 1H, COOH).

EXAMPLE 5

Small Scale Preparation of a Product with Different Proteases

N$_\alpha$-Benzoyl-D-asparagine Ethyl Ester 0.5 g (1.89 mmol) of N$_\alpha$-benzoyl-(D,L)-asparagine ethyl ester (prepared by conventional methods: N-protection in analogy to Zhang et al. (1997), *J. Org. Chem.* 62, 2466; esterification in analogy to example 1) was suspended under vigorous stirring in 23 ml 0.1M sodium chloride solution and 2 ml 0.1M sodium phosphate buffer pH 7.0 in the presence or absence of 4 ml tetrahydrofuran (THF). The pH was adjusted to 6.5 with 1.0N hydrochloric acid and the reaction started by addition of the protease (name, origin and amount see below table). The pH was maintained at 6.5 under vigorous stirring by the controlled addition (pH-static) of 1.0N sodium hydroxide solution. The experiments without THF showing incomplete conversion (see below table) were not worked up, and the experiments with THF were treated as follows: After approximately 50% conversion (corresponds to a consumption of ca. 0.95 ml of 1.0N sodium hydroxide solution) the reaction mixture was extracted with 2×25 ml dichloromethane. The combined organic phases were dried on anhydrous sodium sulfate and evaporated (at 35° C. bath temperature). The residue containing the retained ester was subjected to ee-determination (BGB-176-SE capillary column (15 m×0.25 mm, BGB-Analytik AG, Anwil, Switzerland); H$_2$; 100 kPa; 140–200° C. with 1°/min; inj. 210° C.; det. 220° C.).

| enzyme | THF | conversion | time (h) | e.e. of ester |
|---|---|---|---|---|
| Alkalase 2.4 L (Subtilisin Carlsberg) (Novo) | 50 µl | — | 10% | reaction stops, no workup |
| (Novo) | 50 µl | 4 ml | 53% | 17 | 96.7% |
| Savinase 16 L from *Bacillus sp.* (Novo) | 50 µl | — | 11% | reaction stops, no workup |
| (Novo) | 50 µl | 4 ml | 45% | 46 | 93.2% |
| Protease K from *Tritirachium album* (Fluka 82495) | 2.0 mg | — | 4% | reaction stops, no workup |
| | 4.0 mg | 4 ml | 47% | 23 | 92.0% |

EXAMPLE 6

Large Scale Preparation of a Product Including Subsequent Work-up to Yield also to N$_\alpha$-benzoyl-L-asparagine N$_\alpha$-Benzoyl-D-asparagine Ethyl Ester 3.5 g (13.2 mmol) of N$_\alpha$-benzoyl-(D,L)-asparagine ethyl ester (prepared by conventional methods: N-protection in analogy to Zhang et al. (1997), *J. Org. Chem.* 62, 2466; esterification in analogy to example 1) was suspended under vigorous stirring in 55 ml 0.1M sodium chloride solution and 5 ml 0.1M sodium phosphate buffer pH 7.0 in the presence of 8 ml tetrahydrofuran. The pH was adjusted to 6.5 with 1.0N hydrochloric acid and the reaction started by addition of 350 µl Alkalase 2.4 L [a subtilisin Carlsberg from Novo Nordisk]. The pH was maintained at 6.5 under vigorous stirring by the controlled addition (pH-static) of 1.0N sodium hydroxide solution. After a consumption of 6.44 ml 1.0N sodium hydroxide solution (49% conversion; after 23 h) the reaction mixture was extracted with 3×50 ml dichloromethane and 3×50 ml ethyl acetate. The combined organic phases were dried on anhydrous sodium Sulfate, evaporated (at 35° C. bath temperature) and the residue dried on HV to give 1.63 g of N$_\alpha$-benzoyl-D-asparagine ethyl ester as a white solid (yield: 47%). Enantiomeric excess: 98.2% (Chiralpak-AD, 25 cm×4.6 mm, 75% n-heptane+25% EtOH+0.2% TFA, 1 ml/min, r.t., 220 nm). $[\alpha]_D$=+12.0° (c=1.1; DMSO). ISP-MS: 287.1 (M+Na$^+$), 265.3 (M+H$^+$). HPLC: >99% area. $^1$H-NMR (DMSO): 1.17 (t, 3H, CH$_3$), 2.57–2.72 (stack, 2H, —CH$_2$—), 4.19 (q, 2H, —CH$_2$O—), 4.75 (m, 1H, —CH—), 6.95 (bs, 1H, CONH$_2$), 7.40 (bs, 1H, CONH$_2$), 7.46–7.85 (stack, 5H, Ph), 8.75 (d, 1H, —CONH—).

N$_\alpha$-benzoyl-L-asparagine

The aqueous phase was acidified to pH 2 with 1.0N hydrochloric acid. The white precipitate formed was filtered off and washed with 50 ml 10 mM hydrochloric acid. The filter cake was washed with 25 ml TBME and dried on HV to give 1.28 g of N$_\alpha$-benzoyl-L-asparagine as a white powder (yield: 41%). Enantiomeric excess: >99% (Chiralpak-AD, 25 cm×4.6 mm, 85% n-heptane+15% EtOH+0.12% TFA, 0.7 ml/min, r.t., 220 nm). ISN-MS: 235.2 (M-H$^-$). HPLC: >99% area. $^1$H-NMR (DMSO): 2.57–2.72 (stack, 2H, —CH$_2$—), 4.72 (m, 1H, —CH—), 6.94 (bs, 1H, CONH$_2$), 7.39 (bs, 1H, CONH$_2$), 7.46–7.85 (stack, 5H, Ph), 8.64 (d, 1H, —CONH—), 12.6 (s, 1H, COOH).

EXAMPLE 7

Small Scale Preparation of a Product

$N_\alpha$-Benzoyl-D-asparagine Benzyl Ester 0.5 g (1.53 mmol) of $N_\alpha$-benzoyl-(D,L)-asparagine benzyl ester (prepared by conventional methods: N-protection in analogy to Zhang et al. (1997), *J. Org. Chem.* 62, 2466; esterification via the acid chloride) was suspended under vigorous stirring in 23 ml 0.1M sodium chloride solution and 2 ml 0.1M sodium phosphate buffer pH 7.0 in the presence or absence of 4 ml acetone. The pH was adjusted to 6.5 with 1.0N hydrochloric acid and the reaction started by addition of 50 µl Alcalase 2.4 L [a subtilisin Carlsberg from Novo Nordisk]. The pH was maintained at 6.5 under vigorous stirring by the controlled addition (pH-static) of 1.0N sodium hydroxide solution. After approximately 50% conversion the reaction mixture was extracted with 2×25 ml dichloromethane. The combined organic phases were dried on anhydrous sodium sulfate and evaporated (at 35° C. bath temperature). The residue containing the retained ester was subjected to ee-determination (Chiracel ODH, 15 cm×2.1 mm, 87% n-heptane+13% isopropanol+0.1% TFA, 0.1 ml/min, r.t., 220 nm).

| acetone | conversion (1.0N NaOH consumed) | time (h) | e.e. of ester |
|---------|--------------------------------|----------|---------------|
| none    | 14% (0.21 ml)                  | reaction stops, no workup | |
| 4 ml    | 47% (0.71 ml)                  | 10       | 99.6%         |

EXAMPLE 8

Large Scale Preparation of a Product Including Subsequent Work-up to Yield also to $N_\alpha$-benzoyl-L-asparagine

$N_\alpha$-Benzoyl-D-asparagine Benzyl Ester 2.50 g (7.66 mmol) of $N_\alpha$-benzoyl-(D,L)-asparagine benzyl ester (prepared by conventional methods like in example 10) was suspended under vigorous stirring in 115 ml 0.1M sodium chloride solution and 10 ml 0.1M sodium phosphate buffer pH 7.0 in the presence of 20 ml acetone. The pH was adjusted to 6.5 with 1.0N hydrochloric acid and the reaction started by addition of 250 µl Alcalase 2.4 L [a subtilisin Carlsberg from Novo Nordisk]. The pH was maintained at 6.5 under vigorous stirring by the controlled addition (pH-static) of 1.0N sodium hydroxide solution. After a consumption of 3.479 ml 1.0N sodium hydroxide solution (46% conversion; after 17.9 h) the reaction mixture was extracted with 2×125 ml dichloromethane. The combined organic phases were dried on anhydrous sodium sulfate, evaporated (at 35° C. bath temperature) and the residue triturated in 20 ml TBME overnight. The solid was filtered off and dried on HV to give 1.10 g of $N_\alpha$-benzoyl-D-asparagine benzyl ester as a white solid (yield: 44%). Enantiomeric excess >99% (Chiracel-ODH, 15 cm×2.1 mm, 87% n-heptane+13% iPrOH+0.1% TFA, 0.1 ml/min, r.t.,220 nm). $[\alpha]_D$+13.2°(c= 1.2; DMSO). HPLC: >99% area. ISP-MS: 349.5 (M+Na$^+$), 327.3 (M+H$^+$). $^1$H-NMR (DMSO): 2.61–2.78 (stack, 2H, —CH$_2$—), 4.84 (m, 1H, —CH—),5.14 (s,2H, —OCH$_2$—), 6.97 (bs, 1H, CONH$_2$),7.32–7.84 (stack, 11H, 2×Ph and CONH$_2$),8.83 (d, 1H, —CONH—).

$N_\alpha$-benzoyl-L-asparagine

The aqueous phase was acidified to pH 2 with 25% hydrochloric acid. The formed precipitate was stirred at 1° C. overnight and filtered off. The filter cake was washed with 10 ml 10 mM hydrochloric acid and dried on HV to give 0.77 g of $N_\alpha$-benzoyl-L-asparagine as a white powder (yield: 43%). Enantiomeric excess: >99% (Chiralpak-AD, 25 cm×4.6 mm, 85% n-heptane+15% EtOH+0.12% TFA, 0.7 ml/min, r.t., 220 nm). $[\alpha]_D$=−16.5°(c=1.0; DMSO). HPLC: 99% area. ISN-MS: 235.2 (M-H$^-$) $^1$H-NMR (DMSO): 2.57–2.72 (stack, 2H, —CH$_2$—),4.72 (m, 1H, —CH—), 6.94 (bs, 1H, CONH$_2$),7.39 (bs, 1H, CONH$_2$), 7.46–7.85 (stack, 5H, Ph), 8.64 (d, 1H, —CONH—), 12.6 (s, 1H, COOH).

EXAMPLE 9

Preparation of a Product with Different Solvents

N-Benzyloxycarbonyl-D-asparagine Methyl Ester 2.0 g (7.0 mmol) of N-benzyloxycarbonyl-(D,L)-asparagine methyl ester (98.4%) was suspended under vigorous stirring in 28 ml 0.1M sodium chloride solution, 4 ml 0.1M sodium phosphate buffer pH 7.0 and 8 ml of an organic solvent (see below table; in a reference experiment in the absence of organic solvent 46 ml of sodium chloride solution was usid instead of 28 ml because of pulpy consistency). The pH was adjusted to 6.5 and the reaction started by adding 100 µl Alkalase 2.4 L [a subtilisin Carlsberg from Novo Nordisk]. The pH was maintained at 6.5 under vigorous stirring by the controlled addition (pH-static) of 1.0N sodium hydroxide solution. After a consumption of approximately 3.5 ml of 1.0N sodium hydroxide solution (ca. 50% conversion; see Table) the reaction mixture was extracted with 3×30 ml dichloromethane. The combined organic phases were dried on anhydrous sodium sulfate and evaporated (at 35° C. bath temperature). The residue was triturated overnight in 50 ml tert.butyl methyl ether. The suspension was filtered and the filter cake dried at HV to give 0.84–0.89 g N-benzyloxycarbonyl-D-asparagine methyl ester as a white crystalline powder (see Table). Analytics: see below table (cf. example 2).

| organic solvent | conversion (%) | time (h) | e.e. (%) | HPLC-purity (area %) | yield (mg) (%) |
|-----------------|----------------|----------|----------|----------------------|----------------|
| none            | 13.0           | 1.5      | reaction stops, no workup | | |
| ethanol         | 48.4           | 22.2     | 100      | 97.9                 | 870 (44)       |
| ethyl acetate   | 53.9           | 3.5      | 100      | 100                  | 841 (43)       |
| tert.butyl methyl ether | 47.6   | 5.5      | 97.2     | 100                  | 890 (45)       |
| acetone         | 48.5           | 5.0      | 100      | 100                  | 882 (45)       |

EXAMPLE 10

Preparation of a Product with a Different Protease

N-Benzyloxycarbonyl-D-asparagine Methyl Ester

An experiment with THF as organic solvent was carried out exactly like in Example 9 only that 100 µl Savinase 16 L [an alkaline Bacillus protease from Novo Nordisk]was used instead of 100 µl Alkalase 2.4 L and the reaction was carried out in the absence or in the presence of THF.

| organic solvent | conversion (%) | time (h) | e.e. (%) | HPLC-purity (area %) | yield (mg) (%) |
|---|---|---|---|---|---|
| none | <1 | <0.1 | no appreciable reaction, no workup | | |
| THF | 50.0 | 18.3 | 100 | 100 | 875 (44) |

EXAMPLE 11

Large Scale Preparation of an (L)-asparagine Derivative

N-Benzyloxycarbonyl-(L)-asparagine

In analogy to example 2 10.0 g (35.1 mmol) of N-benzyloxycarbonyl-(D,L)-asparagine methyl ester (98%) was suspended in 140 ml 0.1 M sodium chloride solution, 20 ml 0.1M sodium phosphate buffer pH 6.5 and 40 ml THF under vigorous stirring. 0.5 ml Alkalase 2.4 L was added and the pH maintained at 6.5 under vigorous stirring by the controlled addition (pH-static) of 1.0N sodium hydroxide solution. After a consumption of 16.42 ml of 1.0N sodium hydroxide solution after 2.1 h (corresponds to 47% conversion) the reaction mixture was extracted with 3×200 ml dichloromethane ro remove the uncleaved methyl ester. The aqueous phase was concentrated to approximately 50 ml volume using 200 ml of toluene as entrainer. The pH was adjusted to 3.5 with 25% hydrochloric acid. The formed precipitate was filtered off and triturated overnight in 300 ml of deionized water. The suspension was filtered and the filter cake dried at HV to give 4.07 g of N-benzyloxycarbonyl-L-asparagine as white crystals (yield: 44%). Enantiomeric excess: >99% (Chiracel ODH, 25 cm×4.6 mm, 85% n-heptane+15% isopropanol, 0.8 ml/min, r.t., 220 nm). $[\alpha]_D$=+5.4°(c=2.0; AcOH). ISN-MS: 265.3 (M-H$^-$). HPLC: >99% area. IR (Nujol): 3337,1697,1643,1536,1268,737,695 cm$^-$. $^1$H-NMR (DMSO): 2.41–2.58 (stack, 2H, —CH$_2$—), 4.34 (m, 1H, —CH—), 5.03 (s, 2H, —CH$_2$O—),6.92 (bs, 1H, CONH$_2$), 7.26–7.40 (stack, 6H, Ph and —CONH$_2$), 7.44 (bd, 1H, —OCONH—), 12.67 (bs, 1H, —COOH).

EXAMPLE 12

Small Scale Preparation of a Product

N-benzyloxycarbonyl-(D)-asparagine n-butyl Ester 0.5 g (1.55 mmol) of N-benzyloxycarbonyl-(D,L)-asparagine n-butyl ester (prepared in analogy to Example 1) was suspended under vigorous stirring in 23 ml 0.1M sodium chloride solution and 2 ml 0.1M sodium phosphate buffer pH 7.0 in the presence or absence of 4 ml dioxan. The pH was adjusted to 6.5 with 1.0N hydrochloric acid and the reaction started by addition of 50 µl Alcalase 2.4 L [a subtilisin Carlsberg from Novo Nordisk]. The pH was maintained at 6.5 under vigorous stirring by the controlled addition (pH-static) of 1.0N sodium hydroxide solution. After approximately 50% conversion the reaction mixture was extracted with 2×25 ml dichloromethane. The combined organic phases were dried on anhydrous sodium sulfate and evaporated (at 35° C. bath temperature). The residue containing the retained ester was subjected to ee-determination (Chiracel ODH, 15 cm×0.3 mm, 90% n-heptane+10% isopropanol, 5 µl/min, 30° C., 210 nm).

| dioxan | conversion (1.0N NaOH consumed) | time (h) | e.e. of ester |
|---|---|---|---|
| none | 3% (0.04 ml) | reaction stops, no workup | |
| 4 ml | 51% (0.79 ml) | 48 | 98.4% |

EXAMPLE 13

Large Scale Preparation of a Product

N-benzyloxycarbonyl-(D)-asparagine n-butyl Ester 4.0 g (12.41 mmol) of N-benzyloxycarbonyl-(D,L)-asparagine n-butyl ester (prepared in analogy to Example 1) was suspended under vigorous stirring in 180 ml 0.1M sodium chloride solution and 16 ml 0.1M sodium phosphate buffer pH 7.0 in the presence of 30 ml dioxan. The pH was adjusted to 6.5 with 1.0N hydrochloric acid and the reaction started by addition of 400 µl Alcalase 2.4 L [a subtilisin Carlsberg from Novo Nordisk]. The pH was maintained at 6.5 under vigorous stirring by the controlled addition (pH-static) of 1.0N sodium hydroxide solution. After 66 h and 87 h an additional 200 µl of Alcalase-solution was added to the nearly stopping reaction. After a consumption of 5.73 ml 1.0N sodium hydroxide solution (46% conversion; after totally 91 h) the reaction mixture was extracted with 2×200 ml dichloromethane. The combined organic phases were dried on anhydrous sodium sulfate, evaporated (at 35° C. bath temperature) and the residue triturated overnight in 50 ml TBME. The solid was filtered off, the filter cake washed with TBME and dried on HV to give 1.61 g of N-benzyloxycarbonyl-D-asparagine butyl ester as white solid (yield: 40%). HPLC: 98.9% (area). Enantiomeric excess: 95% (Chiracel ODH, 15 cm×0.3 mm, 90% n-heptane+10% isopropanol, 5 µl/min, 30° C., 210 nm). $[\alpha]_D$+19.9°(c=1.0; DMSO). ISP-MS: 345.3 (M+Na$^+$), 323.3 (M+H$^+$). $^1$H-NMR (DMSO): 0.87 (t, 3H, CH$_3$), 1.31 (m, 2H, —CH$_2$—), 1.52 (m, 2H, —CH$_2$—), 2.43–2.59 (stack, ~2H, —CH$_2$—), 4.03 (m, 2H, —CH$_2$O—), 4.40 (m, 1H, —CH—), 5.03 (m, 2H, —CH$_2$O—),6.93 (bs, 1H, CONH$_2$), 7.29–7.39 (stack, 6H, Ph and CONH$_2$), 7.60 (d, 1H, —CONH—).

What is claimed is:

1. A process for the preparation of D-asparagine derivatives of formula I

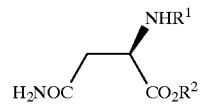

I wherein R$^1$ is an amino protecting group and R$^2$ is an alkyl, a substituted alkyl or a group of formula A R$^3$(OCH$_2$CH$_2$)$_n$—  A wherein R$^3$ is hydrogen or a lower alkyl group and n is 1, 2 or 3, comprising:

a) reacting a compound of formula II

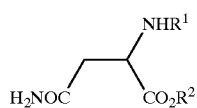

II wherein $R^1$ and $R^2$ are as defined above, with a protease in an aqueous solution at a pH of 6.0–7.5 and an organic solvent, and b) extracting the D-asparagine derivative of formula I.

2. The process according to claim 1, wherein $R^1$ is benzyloxycarbonyl, tert.-butoxycarbonyl, allyloxycarbonyl or benzoyl and $R^2$ is methyl, ethyl, n-propyl, isopropyl, n-butyl, 1-sec-butyl, isobutyl, pentyl or benzyl.

3. The process according to claim 1, wherein the protease is a microbial protease.

4. The process according to claim 3, wherein the microbial protease is a Bacillus protease or subtilisin.

5. The process according to claim 1, wherein the reaction is carried out with one or more organic solvent in a concentration up to 25% v/v.

6. The process according to claim 1, wherein the reaction is carried out at a pH of from 6.0–7.0.

7. The process according to claim 1, wherein the reaction is carried out at a pH of from 6.4–6.6.

8. The process according to claim 1, wherein the organic solvent is tetrahydrofuran, dioxan, tert.-butyl methyl ether, a lower alcohol, ethyl acetate, dimethylsulfoxide, dimethylacetamide, N,N-dimethylformamide or acetone.

* * * * *

UNITED STATES PATENT AND TRADEMARK OFFICE
CERTIFICATE OF CORRECTION

PATENT NO.    : 6,420,166 B2                                          Page 1 of 1
DATED         : July 16, 2002
INVENTOR(S)   : Hans Idling, Mark Rogers-Evans and Beat Wirz It is certified that error appears in the above-identified patent and that said Letters Patent is hereby corrected as shown below:

<u>Title page,</u>
Item [73], delete "Basolea" and insert -- Basilea --.

Signed and Sealed this

Twenty-eighth Day of January, 2003

JAMES E. ROGAN
*Director of the United States Patent and Trademark Office*